United States Patent [19]

Berleth

[11] Patent Number: 4,695,046

[45] Date of Patent: Sep. 22, 1987

[54] SPECIMEN HOLDER CLAMP FOR A MICROTOME

[75] Inventor: Manfred Berleth, Eppelheim, Fed. Rep. of Germany

[73] Assignee: Cambridge Instruments GmbH, Heidelberger, Fed. Rep. of Germany

[21] Appl. No.: 634,928

[22] Filed: Jul. 27, 1984

[30] Foreign Application Priority Data

Jul. 30, 1983 [DE] Fed. Rep. of Germany ....... 3327619

[51] Int. Cl.[4] ............................................. B25B 1/02
[52] U.S. Cl. ..................................... 269/210; 269/244
[58] Field of Search ............... 269/182, 207, 210, 212, 269/244

[56] References Cited

U.S. PATENT DOCUMENTS

| 1,084,489 | 1/1914 | Schmutz | 269/212 |
| 1,415,103 | 5/1922 | McQueen | 269/210 |
| 1,753,924 | 4/1930 | Gordon | 269/182 |
| 2,269,381 | 1/1942 | Robertson | 269/244 |

Primary Examiner—Frederick R. Schmidt
Assistant Examiner—Judy J. Hartman
Attorney, Agent, or Firm—Alan H. Spencer

[57] ABSTRACT

A specimen holder clamp for a microtome comprising a fixed jaw which is fixed relative to a guide member and a movable jaw which is movable along a path defined by the guide member. The clamp is provided with a first infinitely adjustable rack, and the movable jaw carries a second complementary incrementally adjustable rack for coupling engagement so that when the second complementary incrementally adjustable rack engages with the first infinitely adjustable rack, fine adjustment of the clamp can be effected, and when the second complementary incrementally adjustable rack is disengaged, coarse adjustment can be effected. The second complementary incrementally adjustable rack is normally biased into engagement with the first infinitely adjustable rack.

7 Claims, 3 Drawing Figures

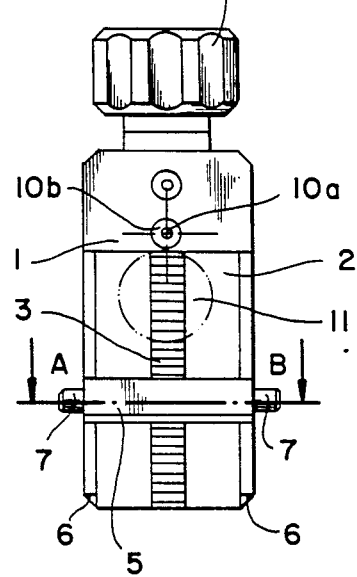
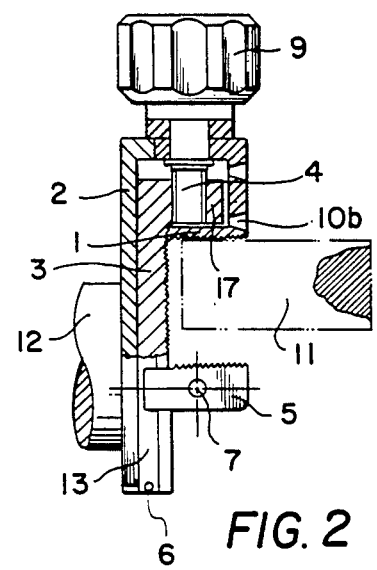
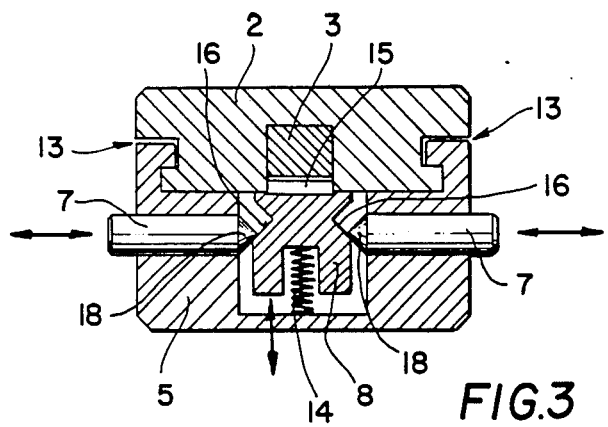

SPECIMEN HOLDER CLAMP FOR A MICROTOME

BACKGROUND OF THE INVENTION

This invention relates to a specimen holder clamp for a microtome, and more particularly, though not exclusively, to a clamp for use with a rotary microtome.

In known clamps for microtomes, particularly for rotary microtomes, a clamp is provided with a threaded spindle on which a movable jaw is mounted. By rotating the threaded spindle, the movable jaw is moved towards or away from a fixed jaw to vary the gripping width between the jaws. Thus, an object, for example, a specimen holder containing a thin-section specimen, can be clamped between these two jaws.

In such known clamps, the cutting direction of a microtome cutter is towards the movable jaw. This means that the mounting of the movable jaw is heavily stressed and is liable to breakdown. The life of the mounting usually determines the useful life of the clamp.

In addition, the clamping of specimen holders is time-consuming since if specimen holders of different sizes are to be clamped successively between the fixed and movable jaws, the dimensional differences of the specimen holders are accommodated by rotating the threaded spindle which can be a tedious operation.

OBJECT OF THE INVENTION

An object of the present invention is to provide a specimen holder clamp for a microtome in which clamping can be accomplished quickly and accurately.

BRIEF DESCRIPTION OF THE INVENTION

According to the present invention, we provide a specimen holder clamp for a microtome having a fixed jaw and a movable jaw. The holder portion for the fixed jaw carries an infinitely adjustable engagement means which cooperates with a complementary adjustable engagement means on the movable jaw. Preferably, the engagement means of the movable jaw is slidably mounted for disengagement from the engagement means of the fixed jaw in order to allow for a coarse adjustment of the spacing between the jaws. In order to accomplish fine adjustment, the engagement means mounted on the fixed jaw is adjustable through an incident position means permitting the movable jaw to be tightened against the specimen holder by urging the engagement means toward the fixed jaw.

The clamp can be adjusted to accommodate widely differing sizes of specimen holders, and the specimen holders can be clamped firmly between the two jaws of the clamp in a simple and rapid manner. The movable jaw can be brought near to a specimen holder to be clamped by sliding it along the path defined by the guide member, and the fine adjustment means can then be used to clamp the specimen holder between the jaws. The movable jaw is precisely guided by the guide member resulting in an improved stability over the known clamps.

In a preferred embodiment, the first engagement element comprises a first infinitely adjustable rack and the second engagement element comprises a second complementary incrementally adjustable rack for coupling engagement. Also, the preferred embodiment utilizes a sawtooth rack formation in order that the clamping force of the movable jaw is applied to planar surfaces perpendicular to the motion of the movable jaw to prevent unintentional disengagement of the racks if a substantial clamping force is used.

Advantageously, biasing means urges the second engagement element into coupling engagement with the first engagement element.

Preferably, release means is operable for uncoupling the second engagement element from the first engagement element against the action of the biasing means.

Preferably, a mark on the first engagement element is visible through an aperture in the guide member when the first engagement element occupies a position which is suitable for the commencement of fine adjustment of the clamp. It can thereby be ensured that the movable jaw, when it has been brought rapidly up to a position adjacent to a specimen holder and after being coupled to the first engagement element, can be finely adjusted by the fine adjustment means to grip the specimen holder firmly between the fixed and the movable jaws.

Clamps, according to the invention, are particularly suitable for use with rotary microtomes, in which case an assembly journal can be attached rigidly to a rear side of the guide member. With an assembly journal which is connected to the rear side of the guide member through a lockable ball and socket joint, the guide member can be easily orientated for cutting.

The movable jaw is preferably placed in front of the fixed jaw in the cutting direction of the associated microtome so that the relatively robust fixed jaw is stressed by the cutting forces rather than the movable jaw.

BRIEF DESCRIPTION OF THE DRAWINGS

Further particulars, features and advantages of the invention will become apparent in the following description of an example of a clamp which is illustrated in the accompanying drawing, wherein:

FIG. 1 is a front elevation of the clamp;

FIG. 2 is a side elevation of the clamp, partly in cross-section; and

FIG. 3 is a cross-section of the clamp along the section line A-B in FIG. 1 on a somewhat larger scale.

DETAILED DESCRIPTION OF THE DRAWINGS

FIGS. 1 and 2 show a clamp which comprises a guide member 2 which is integral with a fixed jaw 1. The guide member comprises a lateral guide means 13 which defines a path along which a jaw 5 is movable towards and away from the fixed jaw. The lateral guide means is shaped to restrain the movable jaw against lateral movement. A first engagement element comprises a first infinitely adjustable rack 3 which is guided by the guide member for movement along a further path defined by the guide member. The fine adjustment means comprises a fine-pitch threaded spindle 4 and the first infinitely adjustable rack 3 includes a portion 17 which is integral with the first infinitely adjustable rack and which defines a threaded bore for receiving the threaded spindle 4. The threaded spindle 4 extends through and is mounted for rotation relative to the guide member 2 by means of a knob 9, mounted on the spindle.

By turning the knob 9, the first infinitely adjustable rack 3, and the movable jaw 5 which moves with the first infinitely adjustable rack, slide relative to the guide member to vary the distance between the fixed jaw and the movable jaw.

FIG. 3 illustrates the manner in which the engagement of the second complementary incrementally adjustable rack is moved into and out of engagement with the first infinitely adjustable rack. The second engagement means comprises a wedge 8 mounted on the movable jaw and having a second complementary incrementally adjustable rack 15 for engagement with the teeth of the first infinitely adjustable rack 3. The second complementary incrementally adjustable rack 15 of the wedge 8 is urged towards the first infinitely adjustable rack by biasing means in the form of a spring 14 which is disposed between the wedge 8 and the movable jaw. In this position, the wedge is restrained against movement relative to the first infinitely adjustable rack, and fine adjustment is effected by moving the first infinitely adjustable rack by means of the threaded spindle 4.

A release means comprises two laterally disposed bolts 7 having conical surfaces 18 which engage in cooperating conical recesses 16 in the wedge 8. When the bolts 7 are pushed inwardly towards one another against the action of biasing means (not shown in the drawings), conical surfaces 18 engage the conical surfaces 16 of the wedge 8 so that the second complementary incrementally adjustable rack 15 is disengaged from the first infinitely adjustable rack 3 against the action of the spring 14.

Before a specimen holder is clamped, the first infinitely adjustable rack is moved to a starting position, as illustrated in FIG. 2. In this position, the portion 17 of the first infinitely adjustable rack 3 is in contact with a rear, upwardly facing surface of the fixed jaw 1. An indicating means for indicating when the first infinitely adjustable rack occupies the starting position is provided by a mark on the first infinitely adjustable rack, in the form of a colored dot 10a, which is visible through a bore 10b, which is designated by a similarly colored mark on the guide member. The knob 9 is turned until the dot 10a becomes visible in the bore 10b. Further indicating means is provided by an upper bore which may be designated by a differently-colored mark, and a mark in a corresponding color on the portion 17, so that, when the dot is not visible in the bore, the further mark is visible in the upper bore.

The movable jaw 5 is movable between the fixed jaw 1 and two stops 6. When the first infinitely adjustable rack 3 has been placed in the starting position, the bolts 7 are pressed towards one another, thereby placing the clamp in a coarse adjustment operating mode and enabling the movable jaw to be slid rapidly towards a position adjacent to the lower edge of the specimen holder to be clamped. The bolts 7 are then released so that the wedge 8 engages with the first infinitely adjustable rack 3 to hold the movable jaw in a fixed position relative to the first infinitely adjustable rack 3. The first infinitely adjustable rack 3 is then moved to move the movable jaw 5 towards the fixed jaw, and towards the specimen holder 11, by rotation of the knob 9 and spindle 4 until the specimen holder 11 is clamped firmly between the fixed and movable jaws. In the embodiment shown, the clamp is mounted on a cylindrical assembly journal 12, which arrangement is particularly suitable for use in a rotary microtome.

In another embodiment of the invention the clamp can be mounted on a ball and socket joint thereby permitting both rotational and angular movement. Ball and socket joints per se are known in the art and are not claimed as part of the invention except when used in conjunction with the clamp of this invention.

I claim:

1. A specimen holder clamp for rotary microtome, comprising
   a guide member,
   a fixed jaw mounted on said guide member,
   a first engagement element coacting with said guide member to permit sliding movement of said first engagement element relative to and along the length of said guide member wherein the relative movement of said first engagement element is guided by said guide member along a first path, said first engagement element defining a fine-pitch threaded bore extending along a second path oriented generally parallel to said first path,
   a rotatable spindle operatively joined to said guide member and coacting with said fine-pitch threaded bore in said first engagement element so that rotation of said spindle relative to said guide member moves said first engagement element relative to said guide member along said first path,
   a movable jaw slidably carried by said first engagement element and positioned in general alignment with said fixed jaw so that movement of said movable jaw relative to said guide member moves said movable jaw toward and away from said fixed jaw,
   a second engagement element interposed between said movable jaw and said first engagement element and defining with said first engagement element complementary engagement surfaces which when in operative engagement with one another fixedly secures said movable jaw to said first engagement element for movement therewith, and
   disengagement means carried by said movable jaw and cooperating with said second engagement element for disengaging said complementary engagement surfaces from one another to permit said movable jaw to be manually moved relative to said first engagement element toward and away from said fixed jaw and thereby permit coarse manual adjustment of said movable jaw and rotation of said rotatable spindle relative to said guide member moves said first engagement element, cooperatively, with said second engagement element to provide fine adjustment of said movable jaw when said first and second engagement elements are engaged.

2. A clamp in accordance with claim 1 wherein said first and second engagement elements include complementary racks.

3. A clamp in accordance with claim 1 wherein said second engagement element includes a wedge slidably mounted in said movable jaw toward and away from said first engagement element, said wedge defining the complementary engagement surface of said first engagement element, and biasing means for urging said wedge into operative engagement with said first engagement element.

4. A clamp in accordance with claim 3 wherein said disengaging means includes means for moving said wedge out of operative engagement with said first engagement element.

5. A clamp in accordance with claim 1 wherein the guide member is rigidly mounted on a microtome specimen arm.

6. A clamp in accordance with claim 1 wherein the guide member is releasably mounted for rotational and angular movement on a specimen arm by means of a ball and socket joint.

7. A clamp in accordance with claim 2 wherein said complementary racks each have a sawtooth configuration.

* * * * *